United States Patent

Van Bommel et al.

Patent Number: 5,219,575
Date of Patent: Jun. 15, 1993

[54] COMPOSITIONS WITH CONTROLLED ZERO-ORDER DELIVERY RATE AND METHOD OF PREPARING THESE COMPOSITIONS

[75] Inventors: Elvira M. G. Van Bommel; Jasper G. Fokkens, both of Weesp, Netherlands

[73] Assignee: Duphar International Research B.V., Weesp, Netherlands

[21] Appl. No.: 570,967

[22] Filed: Aug. 20, 1990

Related U.S. Application Data

[63] Continuation of Ser. No. 212,245, Jun. 27, 1988, abandoned.

[30] Foreign Application Priority Data

Jun. 26, 1987 [NL] Netherlands .................. 8701501
Feb. 22, 1988 [NL] Netherlands .................. 8800432

[51] Int. Cl.$^5$ .................. A61K 9/54; A61K 9/62
[52] U.S. Cl. .................. 424/490; 424/479; 424/480; 424/493; 424/494
[58] Field of Search .............. 424/489, 490, 493, 479, 424/494, 480

[56] References Cited

U.S. PATENT DOCUMENTS

| | | | |
|---|---|---|---|
| 4,289,795 | 9/1981 | Bogentoft et al. | 424/464 |
| 4,341,759 | 7/1982 | Bogentoft et al. | 424/21 |
| 4,457,907 | 7/1984 | Porter | 424/497 X |
| 4,624,848 | 11/1986 | Lee | 424/21 |
| 4,749,576 | 6/1988 | Lee | 424/21 |

FOREIGN PATENT DOCUMENTS

| | | | |
|---|---|---|---|
| 0111144 | 6/1984 | European Pat. Off. | |
| 2103486 | 2/1983 | United Kingdom | 424/490 |

Primary Examiner—Thurman K. Page
Attorney, Agent, or Firm—Stevens, Davis, Miller & Mosher

[57] ABSTRACT

The present invention relates to compositions having a controlled zero-order delivery rate of the active component. The composition comprises a core or a protective layer coated with a continuous matrix of constant composition containing such a mixture of active substance(s) and excipient(s) that the concentration of the active substance(s) decreases from the core or the protective layer towards the outside, and the concentration of the excipient(s) increases in the same direction, whereas the sum of two substantially remains constant over the whole distance.

5 Claims, 1 Drawing Sheet

COMPOSITIONS WITH CONTROLLED ZERO-ORDER DELIVERY RATE AND METHOD OF PREPARING THESE COMPOSITIONS

This application is a continuation of application Ser. No. 212,245, filed Jun. 27, 1988, now abandoned.

The invention relates to a composition with controlled delivery rate of the active component consisting a) of a core of active component and/or inactive component which is coated with an inactive matrix material controlling the release of the active component, and at least one active and one inactive substance, or b) of a film of at least one active component and inactive component(s) incorporated in an inactive matrix material which controls the release of the active component, and is provided on a protective layer.

The rate at which an active substance is released from a pharmaceutical composition is of great importance for the concentration profile of the active substance in the body. The rate at which an active substance is released from a matrix system controlled by diffusion decreases as a function of time. This is because the diffusion pathlength increases. In order to nevertheless reach a zero-order supply delivery rate a concentration gradient of the active substance has been used, which means that the concentration of the active substance increases from the outside towards the core or the protective layer of the composition. In this manner the decrease of the rate at which the active substance is usually released from a matrix system can be corrected for.

A composition having such a concentration gradient of the active substance in the outer layer has been disclosed in German Patent Application 2,651,176. The concentration gradient of the active substance is built up by gradually reducing the concentration of the active substance in the mixture before the coating layer is provided. This has for its result that the composition of the inactive material controlling the delivery rate also varies from the core towards the outside and a discontinuous matrix is formed, which in fact is a barrier coating with the disadvantages involved.

Another method of obtaining a concentration gradient is disclosed by Lee, J.Pharm.Sciences, Vol. 73, No. 10, (1984) pp. 1344–1347. According to this method hydrogel matrices are loaded with active substance. The active substance is then removed partly from the loaded hydrogels in which the active substance is present in a homogeneously distributed manner, by means of a controlled extraction process, which results in hydrogel matrices having a continuous loading gradient of the active substance.

A disadvantage of this complicated method is that, although it is theoretically possible to extract small particles partly, it is doubtful whether this can be carried out on an large scale and in a reproducible manner. Moreover, the delivery rate from hydrogels is controlled not only by diffusion, but other factors are also of importance (for example, the swelling properties of the polymer).

A composition has now been found with controlled zero-order delivery rate which has the advantages of a composition with a matrix system and can be manufactured in a simple manner.

The composition according to the invention is characterised in that the coating layer around the core or on top of the protective layer consists of a continuous matrix of constant composition having therein a mixture of active substance(s) and inactive auxiliary substance(s) which has such a composition that the concentration of the active substance(s) decreases from the core or the protective layer towards the outside of the composition, the concentration of the inactive substance(s) increases in the same direction, the sum of the two substantially remaining constant.

Figure 1:
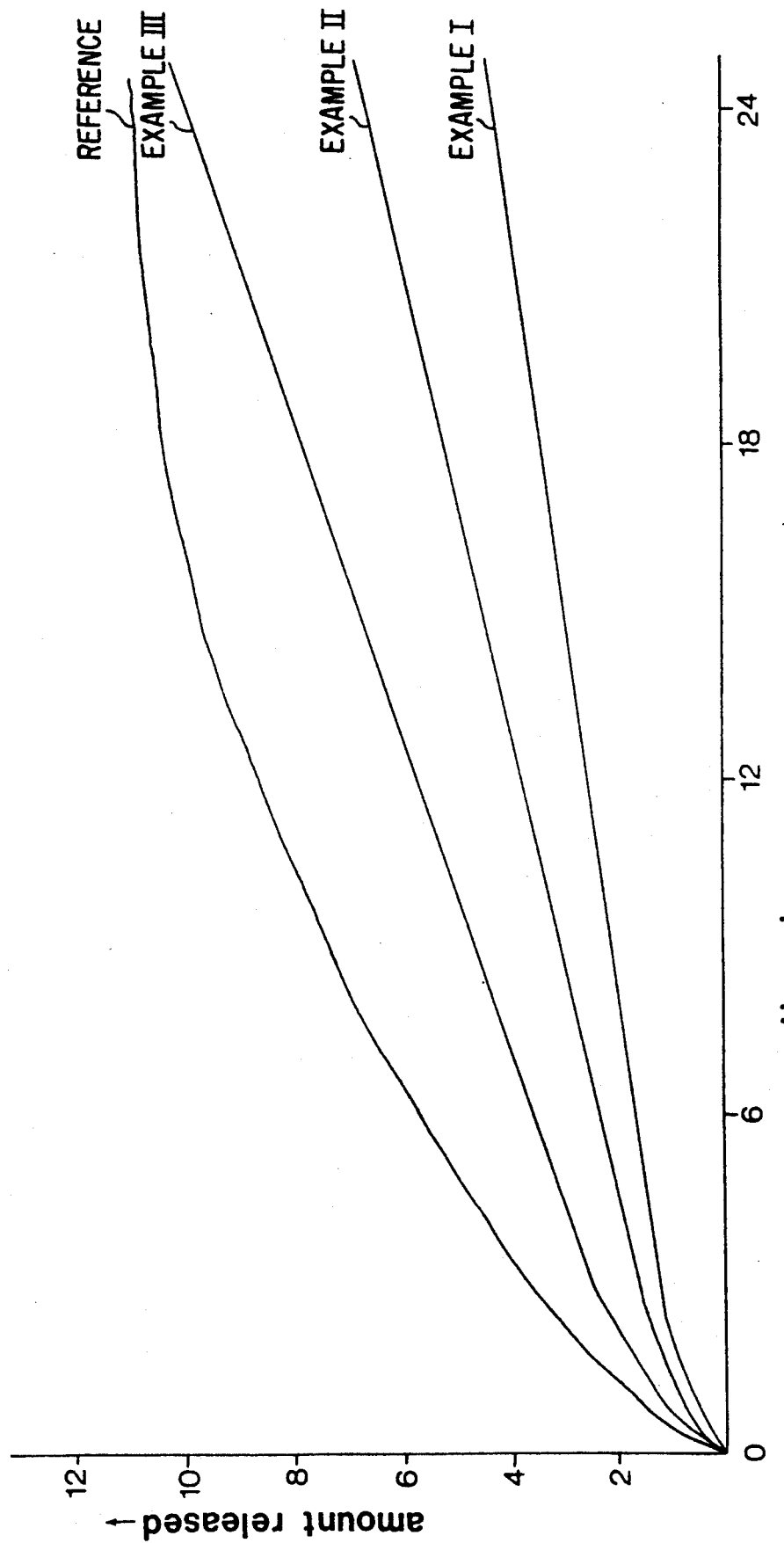
FIG. 1 is a graft of the influence of different concentration gradients on the release of ACE from slabs.

The composition of the cores of the systems according to the invention may vary from 100% of inert material, for example sugar spheres or pvc spheres, to 100% of active substance. Cores are preferably used which consist entirely of inert material.

The conventional substances, for example, polyacrylates, polymethacrylates, celluloses, etc. are to be considered as matrix materials.

The compositions according to the invention may have the form of a granulate the particle size of which is preferably between 250 $\mu$m and 2 mm.

Other forms of composition, however, for example, tablets manufactured from a granulate, or composition forms which are applicable to the skin or mucous membranes, such as TTS, buccal and intranasal forms of application are also possible.

The compositions according to the invention can be manufactured in a simple manner by providing the continuous matrix system and the gradients of active substance(s) and inactive substance(s) on the cores by means of rotor granulation or another form of pellet technology such as coating in a fluidized bed. Preferably, a mixture of continuously varying composition is provided on cores which are present on a rotating plate of a rotor granulator, with the proviso that the quantity of matrix material and the sum of the quantities of active substance(s) and inactive auxiliary material are constant.

Such a method of built-up granulation is particularly suitable for the manufacture of spherical particles having a diameter of at least 250 $\mu$m.

In principle the upper limit of the diameter of the particles is substantially unrestricted, but a realistic upper limit is approximately 2 mm in connection with the passage of the pylorus in vivo.

Non-granular composition forms according to the invention can be obtained, for example, by spraying matrix material, active substance(s) and auxiliary substance(s) on an (inert) surface, a (continuous) gradient being obtained as a result of changes in the concentrations of active substance(s) and auxiliary substance(s). After having been provided with a coating layer and/or adhesive layer the compositions are suitable as controlled delivery systems for application to the skin or mucous membranes.

By suitable choice of carrier material and auxiliary substance(s) any pharmacologically active substance can in principle by formulated according to the invention.

The invention is illustrated by means of the following examples.

EXAMPLE I

In a model slab system flat tablet surfaces were coated in a specially designed apparatus by spraying successively three different ethanolic solutions of a ethylcellulose (EC), acetaminophen (ACE) and xylitol (XYL), thus creating a three-step concentration gradient of acetaminophen and xylitol within the matrix film. The compositions of the three solutions are given in table I.

As a reference matrix films with a uniform distribution of acetaminophen and xylitol were produced in a similar way, the overall concentration of the compounds being equal to those in the gradient system.

The vitro release rate of acetaminophen from both systems was determined (aqueous phase: water, sink conditions).

The results are given in FIG. I. It is evident that the release profile from the gradient system in linear compared with that of the uniform matrix.

EXAMPLE II

Example I was repeated applying a different concentration gradient of acetaminophen and xylitol by using solutions with different compositions (see table I).

The in-vitro release is given in FIG. I, showing that the release rate can be modified by changing the concentration gradient within the system.

EXAMPLE III

Example I was repeated applying a different concentration gradient of acetaminophen and xylitol in the matrix system (see table I). The in vitro release curve is given in FIG. 1, again demonstrating that the release profiles with different slopes are obtained applying the gradient principle.

TABLE A

| MASS FRACTIONS IN THREE-LAYER GRADIENT SYSTEMS | | | |
|---|---|---|---|
| | INNER layer ACE/XYL | MIDDLE layer ACE/XYL | OUTER layer ACE/XYL |
| example I | 3.33/1.00 | 1.83/1.50 | 0.33/3.00 |
| example II | 3.33/0.50 | 1.33/1.67 | 0.50/3.00 |
| example III | 3.33/1.83 | 2.08/1.75 | 0.33/3.25 |
| reference | 1.91/1.83 | 1.91/1.83 | 1.91/1.83 |

Mass fraction of EC in each layer: 3.33

We claim:

1. A composition with controlled delivery rate of the active component consisting a) of a core of active substance and/or inactive component which is coated with an inactive matrix material controlling the release of the active component, and at least one active and one inactive substance, or b) of a film of at least one active component and inactive component(s) incorporated in an inactive matrix material which controls the release of the active component, and is provided on a protective layer, characterised in that the layer around the core or on top of the protective layer consists of a continuous matrix of constant composition having therein such a mixture of active substance(s) and inactive auxiliary substance(s) that the concentration of the active substance(s) decreases from the core or the protective layer towards the outside of the composition, the concentration of the inactive auxiliary substance(s) increases in the same direction, the sum of the two substantially remaining constant.

2. A composition as claimed in claim 1, characterised in that it comprises (spherical) particles having a diameter of 250 $\mu$m to 2 mm.

3. A composition according to claim 1, characterised in that it is a composition for application on the skin or on mucous membranes.

4. A method of manufacturing a composition as claimed in claim 1, characterized in that a continuous matrix is provided by means of a rotor granulator or coating in a fluidized bed loaded with a concentration of active substance(s) decreasing from the core towards the outside and a concentration of inactive soluble auxiliary substance(s) increasing in the same direction, the sum of the two being substantially constant.

5. A method as claimed in claim 4, characterised in that the matrix materials, active substance(s) and auxiliary substance(s) are sprayed on an (inert) surface, the concentrations of the active substance(s) and auxiliary substance(s) being continuously changed.

* * * * *